(12) United States Patent
Oon et al.

(10) Patent No.: US 6,787,142 B2
(45) Date of Patent: Sep. 7, 2004

(54) MUTANT HUMAN HEPATITIS B VIRAL STRAIN AND USES THEREOF

(75) Inventors: Chong Jin Oon, Singapore (SG); Gek Keow Lim, Singapore (SG); Yi Zhao, Singapore (SG); Wei Ning Chen, Singapore (SG)

(73) Assignee: Government of Republic of Singapore, Singapore (SG)

( * ) Notice: Subject to any disclaimer, the term of this patent is extended or adjusted under 35 U.S.C. 154(b) by 0 days.

(21) Appl. No.: 10/209,264

(22) Filed: Jul. 31, 2002

(65) Prior Publication Data

US 2003/0003111 A1 Jan. 2, 2003

Related U.S. Application Data

(62) Division of application No. 09/719,528, filed as application No. PCT/SG98/00046 on Jun. 19, 1998, now Pat. No. 6,558,675.

(51) Int. Cl.[7] .................. A61K 39/29; A61K 39/42; C07K 14/00; C07K 14/01; C07K 14/18

(52) U.S. Cl. .................. 424/189.1; 530/300; 530/350; 530/24.3; 530/24.32; 530/23.7; 530/23.72; 424/184.1; 424/185.1; 424/227.1; 435/5; 435/6; 435/8; 435/9.1

(58) Field of Search .................. 424/185.1, 186.1, 424/189.1, 227.1; 530/350, 300

(56) References Cited

FOREIGN PATENT DOCUMENTS

| WO | 9521189 | 8/1995 |
|---|---|---|
| WO | 9811916 | 3/1998 |

OTHER PUBLICATIONS

Galibert, F., et al. "Nucleotide Sequence of a Cloned Woodchuck Hepatitis . . . " Journal of Virology (1982) vol. 41 pp 51–65.

Takeshima, H., et al. "Structural Analysis of the Gene Coding for Hepatitis B Virus Surface Antigen and its Product" Journal of General Virology (1985) vol. 66 pp 195–200.

Fujiyama, A., et al. "Cloning and Structural Analyses of Hepatitis B Virus DNAs, Subtype adr" Nucleic Acids Research (1983) vol. 11, No. 13 pp 4601–4610.

Norder, H., et al. "Genetic Relatedness of Hepatitis B Viral Strains of Diverse Geographical Origin . . . " Journal of General Virology (1993) vol. 74 pp 1341–1348.

Don Ganem, Fields, Virology Third Edition, (1996) vol. 2 pp 2741–2447.

Primary Examiner—James Housel
Assistant Examiner—Bao Qun Li
(74) Attorney, Agent, or Firm—Ladas & Parry (57) ABSTRACT

This invention provides an isolated strain of Hepatitis B virus designated Human Hepatitis B Virus Surface Antigen-'S'-133 Oon Strain (Methionine to Threonine) which constituent viral genome is deposited under Accession Nos. P97121501, P97121502 and P97121503 with the European Collection of Cell Culture on 15th December 1997. This invention also provides an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine. This invention also provides an isolated nucleic acid which encodes a peptide, wherein the peptide is encoded by a nucleic acid molecule comprising nucleotides 527 through 595 of SEQ. I.D. No. 1 and the purified peptide. This invention also provides various methods of using the disclosed isolated nucleic acid and peptides.

2 Claims, 2 Drawing Sheets

MUTANT HUMAN HEPATITIS B VIRAL STRAIN AND USES THEREOF

This application is a divisional of application Ser. No. 09/719,528 filed on Apr. 30, 2001 now U.S. Pat. No. 6,558,675 which is a 371 of International Application PCT/SG98/00046 filed on Jun. 19, 1998, which designated the U.S., claims the benefit thereof and incorporates the same by reference.

Throughout this application, various references are referred to within parentheses. Disclosures of these publications in their entireties are hereby incorporated by reference into this application to more fully describe the state of the art to which this invention pertains.

BACKGROUND OF THE INVENTION

The present invention concerns the human hepatitis B virus genome, isolated from hepatocellular carcinoma (HCC), and with a mutation at amino acid residue 133 (Methionine to Threonine) within the major surface antigen, its nucleotide sequence, the deduced amino acid sequence of the four major proteins, antigen, antibody, detection systems, development of effective vaccines, and antiviral agents.

HCC is one of the most common human liver cancers, particularly in Asia where 70% of the worldwide new cases are found every year. It usually arises in cirrhotic livers as a complication of chronic liver disease. The clinical manifestations of HCC patients are unspecific with signs and symptoms only appearing in the later stages of the cancer.

One of the major causes of chronic liver diseases is hepatitis B viral infection. First discovered in 1963 as a human virus that is transmitted parenterally, chronic hepatitis B viral infection has been most commonly implicated in serological undefined pathogenesis of HCC. Despite the fact that hepatitis B virus does not display features of a complete viral oncogene, its involvement in the development of HCC can be attributed to various aspects of its interaction with host hepatocyte cells. These include the promiscuous transcriptional activity of the smallest viral protein, X, which enhances the expression level of many cellular target genes including proto-oncogenes. On the other hand, integrated viral DNA in the host chromosomes is regularly found in HCC patients. There is also evidence for an active role in the development of HCC by the major surface antigen. This protein has served as the main detection marker for carriers of hepatitis B virus. The most antigenic epitope is a highly conserved region spanning 23 amino acid residues and located from amino acid position 124 to 147 of the major surface antigen. This small region designated as the group specific determinant "a" is found in all subtypes and isolates of hepatitis B viral genomes. Its antigenic properties seem due to its proposed double loop structure, to which the vaccine-induced neutralizing antibody binds.

Our epidemiological data indicate that the wild type major surface antigen has been found in most HCC patients. Furthermore, observation indicates that several variants of the major surface antigen from HCC patients may be involved in the pathogenesis of HCC. Direct sequencing analysis indicated that 24 out of 63 HCC patients (around 38%) carry various mutations in the "a" epitope of the major surface antigen. When both the wild type and variant cases are combined, the proportion of the variant virus carrying a mutation at amino acid residue 133, located in the first loop of the "a" epitope of the major surface antigen (Methionine to Threonine), is as high as 12.7% in 63 HCC patients from the Southeast Asia region, and present in 5 local HCC cases. However, the same mutation is found in only 2% of hepatitis B virus carriers in a random population (more than 100 cases). The significance of this variant at amino acid residue 133 is further strengthened by the fact that the proportion of variant virus at amino acid residue 145 (Glycine to Arginine), better known as a vaccine-induced mutant and located in the second loop of the "a" epitope, remains constant at 8% in hepatitis B virus carriers in the random population sample.

Although this variant hepatitis B viral strain, carrying a mutation at amino acid residue 133 (Methionine to Threonine) of the major surface antigen in HCC patients, may arise differently from those induced following vaccination (i.e. with a mutation at amino acid residue 145 of the major surface antigen), this strain shares similar characteristics in that both are stable and cases of vertical transmission of these strains have been reported, despite effective hepatitis B virus prophylaxis and hepatitis B immunoglobulin (HBIG) being used.

The emergence of the variant human hepatitis B virus, carrying mutations in the "a" epitope of the major surface antigen, in HCC is of concern. The high proportion of the mutant virus with a substitution at amino acid residue 133 of the major surface antigen is of particular interest as it may point to a close association with the pathogenesis of HCC. This correlation would therefore require the urgent development of specific detection systems as well as effective prophylactic and therapeutic vaccines and antiviral agents. Determination of the nucleotide sequence of this mutant virus constitutes the first step towards these aims and will certainly be helpful for developing the above-mentioned diagnostic and treatment schemes.

SUMMARY OF THE INVENTION

This invention provides an isolated strain of Hepatitis B virus designated Human Hepatitis B Virus Surface Antigen-'S'-133 Oon Strain (Methionine to Threonine) which constituent viral genome is deposited under Accession Nos. P97121501, P97121502 and P97121503 with the European Collection of Cell Culture on Dec. 15, 1997.

This invention further provides an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine.

This invention further provides a method of producing the polypeptide and a method of obtaining the polypeptide in purified form so as to recover a purified polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine.

This invention further provides an oligonucleotide of at least 15 nucleotides capable of specifically hybridizing with sequences of only the mutant viral strain of hepatitis B virus.

This invention further provides a method of obtaining antibodies to the polypeptide and to the antibodies produced.

This invention also provides use of the above-identified nucleic acid, polypeptide, peptide or antibody for determining whether a subject is infected with the above-identified viral strain.

This invention also provides use of the above-identified nucleic acid, polypeptide, peptide or antibody for determining whether a subject has a predisposition for hepatocellular carcinoma.

This invention also provides a vaccine for preventing and treating hepatocellular carcinoma, as well as, a vaccine for treating or preventing infection by the above-identified mutant strain of hepatitis B virus.

This invention also provides a method for identifying a chemical compound which is capable of treating or preventing hepatocellular carcinoma and compositions containing such compounds.

This invention also provides a method for identifying a chemical compound which is capable of treating or preventing infection by the above-identified mutant strain and compositions containing such compounds.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

C=cytosine A=adenosine
T=thymidine G=guanosine

The present invention provides the nucleotide sequence of human hepatitis B virus genome isolated from hepatocellular carcinoma (HCC), which carries a mutation at amino acid residue 133 (Methionine to Threonine) of the major surface antigen, consisting of 3215 nucleotides coding for 4 overlapping viral proteins.

The invention provides the amino acid sequences of the four major viral proteins, including the DNA polymerase, large/middle/major surface antigen, core and transactivating X. These proteins can be produced using recombinant technology, and used in developing polyclonal or monoclonal antibodies.

The present invention also provides a human hepatitis B virus diagnostic system, specific for the mutation at amino acid residue 133 (Methionine to Threonine) of the major surface antigen, using the nucleotide or protein sequences, or antibodies described above.

This invention provides an isolated strain of Hepatitis B virus designated Human Hepatitis B Virus Surface Antigen-'S'-133 Oon-Strain (Methionine to Threonine) which constituent viral genome is deposited under Accession Nos. P97121501, P97121502 and P97121503.

This invention also provides an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine. In a specific embodiment, the polypeptide is being encoded by nucleotides 155 through 835 of the nucleic acid sequence designated SEQ. I.D. No. 1, comprising nucleotides "ATG" in position 551–553, instead of "ACG."

The isolated nucleic acid can be DNA or RNA, specifically cDNA or genomic DNA.

In another embodiment, the polypeptide has an amino acid sequence substantially identical to amino acid residues 174 through 400 of the amino acid sequence designated SEQ. I.D. No. 3.

This invention also provides an isolated nucleic acid which encodes a peptide, wherein the peptide is encoded by a nucleic acid molecule comprising nucleotides 527 through 595 of SEQ I.D. No. 1.

This invention also provides an isolated nucleic acid which encodes a peptide, wherein the peptide has an amino acid sequence comprising amino acid residues 298 through 320 of the amino acid sequence designated SEQ. I.D. No. 3.

This invention further provides a vector comprising an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine and operatively linked to a promoter of RNA transcription.

This invention further provides a vector comprising an isolated nucleic acid encoding a peptide, wherein the peptide is encoded by a nucleic acid molecule comprising nucleotides 527 through 595 of SEQ. I.D. No. 1.

Specifically the vectors-above comprise viral DNA.

This invention also provides a host vector system for the production of a polypeptide or peptide and comprises the above-identified vectors in a suitable host.

Also in this invention, is a method of producing a polypeptide which comprises growing in the host vector systems described above, under suitable conditions permitting production of the polypeptide or the peptide and recovering the polypeptide or peptide.

This invention also provides a method of obtaining a polypeptide or peptide in purified form which comprises: (a) introducing any of the above-describes vectors into a suitable host cell; (b) culturing the resulting host cell so as to produce the polypeptide; (c) recovering the polypeptide produced into step (b); and (d) purifying the polypeptide or peptide so recovered.

This invention also provides a purified polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine. Specifically, one can obtain the purified polypeptide or peptide using the above methods.

This invention provides a purified peptide, wherein the peptide has an amino acid sequence comprising amino acid residues 298 through 320 of the amino acid sequence designated SEQ. I.D. No. 3.

This invention also provides an oligonucleotide of at least 15 nucleotides capable of specifically hybridizing with a unique sequence of nucleotides within a nucleic acid which encodes a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine rather than a methionine, without hybridizing to any sequence of nucleotides within a nucleic acid which encodes the major surface antigen of a wildtype hepatitis B virus. In an embodiment, the oligonucleotide comprises nucleotides 527 through 595 of SEQ. I.D. No. 1.

This invention also provides a composition capable of stimulating or enhancing antibody production for the polypeptide.

This invention also provides a method of obtaining antibodies to a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, and not to the major surface antigen of a wild type hepatitis B virus, comprising: (a) obtaining the polypeptide in a purified form; (b) immunizing an organism capable of producing antibodies against the purified polypeptide; (c) collecting the produced antibodies; (d) combining the produced antibodies and the purified polypeptide under conditions to form a complex; and (e) determining which produced antibodies form a complex with the purified polypeptide so as to obtain antibodies to the polypeptide. In a specific embodiment, the polypeptide is being encoded by nucleotides 155 through 835 of the nucleic acid sequence designated SEQ. I.D. No. 1. In another embodiment, the polypeptide has an amino acid sequence substantially identical to amino acid residues 174 through 400 of the amino acid sequence designated SEQ. I.D. No. 3.

One can obtain these antibodies from organism such as a rabbit or a mouse.

This invention also provides a method of obtaining antibodies to a peptide, wherein the peptide has an amino acid sequence comprising amino acid residues 298 through 320 of the amino acid sequence designated SEQ. I.D. No. 3, comprising: (a) obtaining the peptide in a purified form; (b) immunizing an organism capable of producing antibodies against the purified peptide; (c) collecting the produced antibodies; (d) combining the produced antibodies and the purified peptide under conditions to form a complex; and (e) determining which produced antibodies form a complex with the purified peptide so as to obtain antibodies to the peptide.

This invention also provides for the antibodies obtained using the methods described above, specifically when the antibodies are monoclonal antibodies.

This invention also provides for antibodies capable of detecting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, and incapable of detecting the major surface antigen of a wild type hepatitis B virus.

This invention further provides for antibodies capable of detecting a peptide, wherein the peptide has an amino acid sequence comprising amino acid residues 298 through 320 of the amino acid sequence designated SEQ. I.D. No. 3.

This invention provides use of a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine for determining whether a subject is infected with a strain of Hepatitis B virus designated Human Hepatitis B Virus Surface Antigen-'S'-133 Oon Strain (Methionine to Threonine), wherein such determination comprises: (a) obtaining an appropriate nucleic acid sample from the subject; and (b) determining whether the nucleic acid sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine.

In one embodiment, the nucleic acid sample in step (a) comprises mRNA corresponding to the transcript of DNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, and wherein the determining of step (b), which comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes the polypeptide.

In another embodiment, the nucleic acid sample in step (a) comprises mRNA corresponding to the transcript of DNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, and wherein the determining of step (b) comprises: (i) translating the mRNA under suitable conditions to obtain an amino acid sequence; and (ii) comparing the amino acid sequence of step (i) with the amino acid sequence encoded by the above-described isolated nucleic acid so as to thereby determine whether the nucleic acid sample is, or is derived from, a nucleic acid which encodes the polypeptide.

Further, one can determine step (b) by: (i) amplifying the nucleic acid present in the sample of step (a); and (ii) detecting the presence of polypeptide in the resulting amplified nucleic acid.

This invention also provides use of antibodies that recognize a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine for determining whether a subject is infected with a strain of Hepatitis B virus designated Human Hepatitis B Virus Surface Antigen-'S'-133 Oon Strain (Methionine to Threonine), wherein such determination comprises: (a) obtaining an appropriate sample from the subject; and (b) determining whether the sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine by contacting the sample under appropriate conditions to bind to the antibodies recognizing the polypeptide so as to determine whether a subject is infected.

In the above-identified uses, the isolated nucleic acid, oligonucleotide or antibody may be labeled with a detectable marker. Examples of detectable markers include radioactive isotopes, fluorophors, and enzymes.

In embodiments, the sample may comprise blood, tissue or sera.

This invention provides use of a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine for determining whether a subject has a predisposition for hepatocellular carcinoma, wherein such determination comprises: (a) obtaining an appropriate nucleic acid sample from the subject; and (b) determining whether the nucleic acid sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine.

In one embodiment, the nucleic acid sample in step (a) comprises mRNA corresponding to the transcript of DNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, and wherein the determining of step (b), which comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes the polypeptide.

In another embodiment, the nucleic acid sample in step (a) comprises mRNA corresponding to the transcript of DNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, and wherein the determining of step (b) comprises: (i) translating the mRNA under suitable conditions to obtain an amino acid sequence; and (ii) comparing the amino acid sequence of step (i) with the amino acid sequence of the isolated nucleic acid which encodes a polypeptide, wherein the polypeptide has an amino acid sequence substantially identical to amino acids 174 through 400 of the amino acid sequence designated SEQ. I.D. No. 3, so as to thereby determine whether the nucleic acid sample is, or is derived from, a nucleic acid which encodes the polypeptide.

In another embodiment, the determining of step (b) comprises: (i) amplifying the nucleic acid present in the sample of step (a); and (ii) detecting the presence of polypeptide in the resulting amplified nucleic acid.

This invention further provides use of antibodies that recognize a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine for determining whether a subject has a predisposition for hepatocellular carcinoma, wherein such determination comprises: (a) obtaining an appropriate sample from the subject; and (b) determining whether the sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine by contacting the sample under appropriate conditions to bind to the antibodies that recognize the polypeptide so as to determine whether a subject is infected.

In the above-described uses, the isolated nucleic acid, oligonucleotide or antibody may be labeled with a detectable marker. Examples of detectable markers include radioactive isotopes, fluorophors, and enzymes.

In embodiments, the sample may comprise blood, tissue or sera.

This invention provides a method for identifying a chemical compound for the manufacture of a medicament which is capable of treating infection by a strain of Hepatitis B virus designated Human Hepatitis B Virus Surface Antigen-'S'-133 Oon Strain (Methionine to Threonine) which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, with the chemical compound under conditions permitting binding between the polypeptide and the chemical compound; (b) detecting specific binding of the chemical compound to the polypeptide; and (c) determining whether the chemical compound inhibits the polypeptide so as to identify a chemical compound which is capable of treating infection by the viral strain.

This invention also provides a method for identifying a chemical compound for the manufacture of a medicament which is capable of preventing infection by a strain of Hepatitis B virus designated Human Hepatitis B Virus Surface Antigen-'S'-133 Oon Strain (Methionine to Threonine), which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, with the chemical compound under conditions permitting binding between the polypeptide and the chemical compound; (b) detecting specific binding of the chemical compound to the polypeptide; and (c) determining whether the chemical compound inhibits the polypeptide so as to identify a chemical compound which is capable of preventing infection by the viral strain.

This invention also provides a method for identifying a chemical compound for the manufacture of a medicament which is capable of treating hepatocellular carcinoma which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, with the chemical compound under conditions permitting binding between the polypeptide and the chemical compound; (b) detecting specific binding of the chemical compound to the polypeptide; and (c) determining whether the chemical compound inhibits the polypeptide so as to identify a chemical compound which is capable of treating infection by the viral strain.

This invention also provides a method for identifying a chemical compound for the manufacture of a medicament which is capable of preventing hepatocellular carcinoma, which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, with the chemical compound under conditions permitting binding between the polypeptide and the chemical compound; (b) detecting specific binding of the chemical compound to the polypeptide; and (c) determining whether the chemical compound inhibits the polypeptide so as to identify a chemical compound which is capable of preventing infection by the viral strain.

This invention also provides a composition comprising the chemical compound identified by the above-described methods in an amount effective to treat or prevent infection by the strain and a pharmaceutically effective carrier.

This invention provides a composition comprising a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine, or derivative thereof, the amounts of such polypeptide being effective to stimulate or enhance antibody production in a subject, and a pharmaceutically acceptable carrier.

The actual effective amount will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. Use of an adjuvant for example, would lower the required amount of the polypeptide. One of skill in the art could routinely perform empirical activity tests to determine the bioactivity in bioassays and thus determine the effective amount.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention also provides a composition comprising a peptide, wherein the peptide has an amino acid sequence comprising amino acid residues 298 through 320 of the amino acid sequence designated SEQ. I.D. No. 3 or derivative thereof, the amounts of such peptide being effective to stimulate or enhance antibody production in a subject, and a pharmaceutically acceptable.

This invention also provides compositions comprising the chemical compound identified by the above-described methods in an amount effective to treat or prevent hepatocellular carcinoma and a pharmaceutically effective carrier.

This invention also provides a composition comprising the chemical compound identified by the above-described methods in an amount effective to treat or prevent infection by a strain of hepatitis B virus designated Human Hepatitis B Virus Surface Antigen-'S'-133 Oon Strain (Methionine to Threonine) and a pharmaceutically effective carrier.

This invention further provides use of the above-identified compositions for treating a subject infected with a strain of Hepatitis B virus designated Human Hepatitis B Virus Surface Antigen-'S'-133 Oon Strain (Methionine to Threonine).

This invention also provides use of the above-identified compositions for preventing infection by a strain of Hepatitis B virus designated Human Hepatitis B Virus Surface Antigen-'S'-133 Oon Strain (Methionine to Threonine) in a subject.

This invention also provides use of the above-described compositions for treating or preventing hepatocellular carcinoma.

This invention also provides a method of screening bodily fluids from a subject for a strain of hepatitis B virus designated Human Hepatitis B Virus Surface Antigen-'S'-133 Oon Strain (Methionine to Threonine) which comprises: (a) obtaining an appropriate sample of bodily fluid from the subject; (b) determining the presence of a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 133 of such polypeptide is a threonine, rather than a methionine in the sample of step (a) so as to screen the sample for the strain. Specifically, wherein the bodily fluid comprises blood, sera, or a nucleic acid sample of blood or sera.

This invention further provides a method of treating a subject infected with this viral strain.

This invention also provides a method of screening tissues and bodily fluids for this viral strain.

This invention provides a hepatitis vaccine, comprising a mutant form of the surface antigen of hepatitis B virus, such polypeptide having an amino acid sequence which differs from the wild type amino acid sequence of the major surface antigen of hepatitis B in that the amino acid at position number 133 of such polypeptide is a threonine rather than a methionine.

This invention also provides the above-described vaccine, further comprising an adjuvant.

This invention is illustrated in the Experimental Details section which follows. These sections are set forth to aid in an understanding of the invention but are not intended to, and should not be construed to, limit in any way the invention as set forth in the claims which follow thereafter.
Experimental Details In the method described below, the human hepatitis B virus carrying the mutation at amino acid residue 133 (Methionine to Threonine) of the major surface antigen was isolated, and its nucleotide sequence was determined.

Serum sample (5194) was obtained from a 63-year old Chinese female patient of surface antigen carrier. She was confirmed as a HCC patient by subsequent biopsy. The hepatitis B virus from her serum carried a mutation at amino acid residue 133 (Methionine to Threonine) in the major surface antigen, as shown by previous sequencing analysis of the "a" epitope. Viral DNA was extracted prior to the determination of its sequence in the present invention.

As described in the examples below, the genome of this hepatitis B mutant virus from HCC and carrying a mutation at the amino acid residue 133 of the major surface antigen, consists of 3215 nucleotides which is identical to that of the wild type virus of the same subtype (adr). Open reading frames (ORF) coding for the major viral proteins are found at corresponding positions when compared to the wild type virus. Position 1 in the mutant hepatitis B virus genome is defined according to that in the wild type virus.

Figure 1:
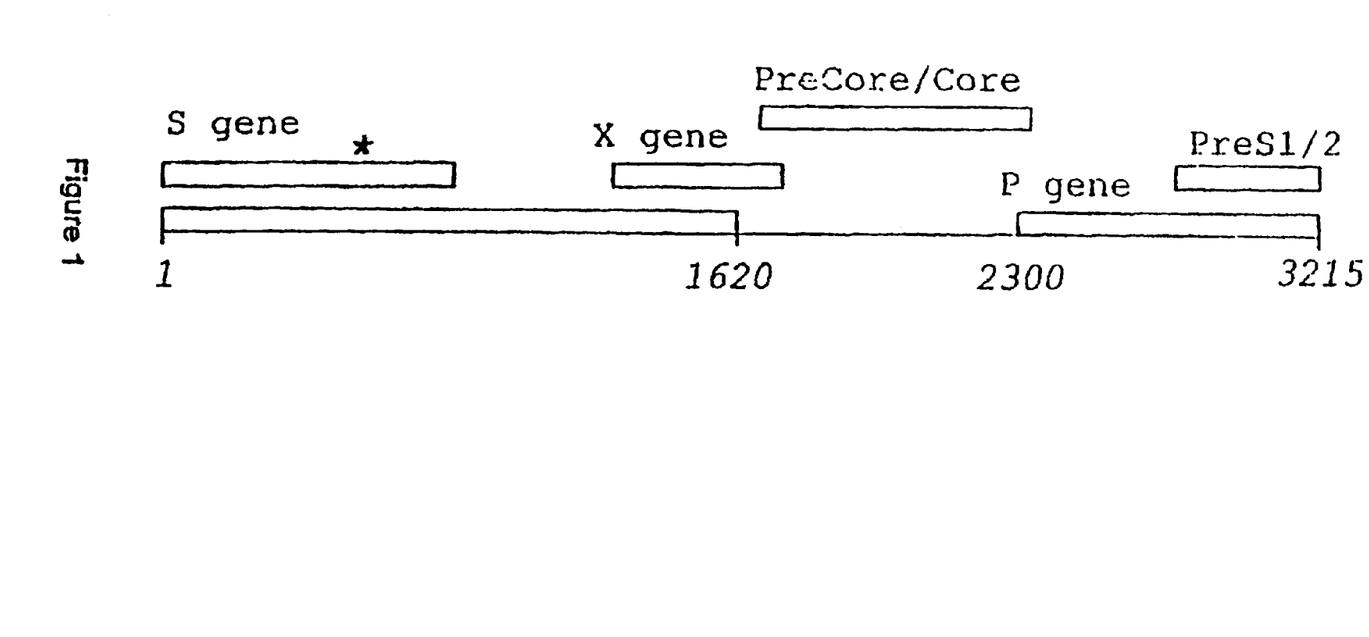
FIG. 1. Structure of the four open reading frames of human hepatitis B viral genome isolated from HCC (with a Methionine to Threonine mutation at amino acid residue 133 of the major surface antigen, as labeled by an asterisk). The major viral proteins: DNA polymerase, large/middle/major surface antigen, precore, core and transactivating X are denoted as P, PreS 1/PreS2/S, PreC, C and X respectively.

The structure of the different ORFs in the mutant human virus genome are reported here and summarized in FIG. 1. The locations are indicated as follows:

DNA polymerase gene starts at position 2307 and ends at position 1623, therefore consisting of 2532 nucleotides and coding for 843 amino acid residues;

Large surface antigen gene starts at position 2848 and ends at position 835, therefore consisting of 1203 nucleotides and coding for 400 amino acid residues. This large surface antigen overlaps the middle surface antigen which starts at position 3205 and the major surface antigen which starts at position 155. Both the middle (consisting of 281 amino acids residues) and the major (consisting of 226 amino acid residues) surface antigens end at the same position as the large surface antigen;

Core gene starts at position 1814 and ends at position 2452, therefore consisting of 639 nucleotides and coding for 212 amino acid residues; and Trans-activating X gene starts at position 1374 and ends at position 1838, therefore consisting of 465 nucleotides and coding for 154 amino acid residues.

Furthermore, sequence analysis has established this mutant hepatitis B virus belongs to the adr subtype as indicated by a lysine residue and an arginine residue at positions 122 and 160 respectively in the major surface antigen. Consistent with previous analysis of the "a" epitope by direct sequencing, the mutation (from Methionine to Threonine) is found at amino acid residue 133 of the major surface antigen.

Compared with the wild type hepatitis B virus deposited in the Genbank database (accession number D16665), the identity of this hepatitis B viral strain is at 90.3% for the nucleotide sequence. The identity of different viral proteins of the present mutant hepatitis B virus as compared with its counterpart, the wild type virus, is 95.8%, 97.5%, 95.1% and 94.8% for DNA polymerase (PIR—Protein Identification Resources accession number S43491), large surface antigen (PIR accession number JQ2107), core (PIR accession number S43490) and trans-activating X (PIR accession number S35529) proteins respectively. Conversely, numerous amino acid substitutions are present in each of the viral proteins as compared to their wild type counterparts, these include: 5 mutations in DNA polymerase, 5 in large surface antigen (including the Methionine to Threonine change for the initiation codon of the major surface antigen), 5 in core and 4 in trans-activating X protein.

The human hepatitis B virus genome in the present invention, isolated from HCC and carrying mutation at amino acid residue 133 (Methionine to Threonine) of the major surface antigen, can be used as material to design oligonucleotides specific to the mutant virus genome. These oligonucleotides can be used as material for highly specific diagnostic agents that detect virus derived from HCC carrying a mutation at amino acid residue 133 of the major surface antigen.

The human hepatitis B virus genome in the present invention, with a mutation at amino acid residue 133 (Methionine to Threonine) of the major surface antigen, can be used as material to produce proteins of the invention by expressing a vector that carries the relevant coding region, and which can replicate in a host cell such as Escherichia coli by standard DNA recombinant technology.

Proteins of the present invention are useful as material for highly specific diagnostic agents capable of detecting hepatitis B virus from HCC, carrying a mutation at amino acid residue 133 (Methionine to Threonine) of the major surface antigen. Using known methods, these same proteins can be used to produce polyclonal and monoclonal antibodies.

Polyclonal and monoclonal antibodies can be used as material for diagnostic agents to detect with high specificity antigens of hepatitis B virus, from HCC, with a mutation at amino acid residue 133 (Methionine to Threonine) of the major surface antigen.

A detection system using each protein of the present invention or proteins with partial replacement of amino acids, and a detection system using monoclonal or polyclonal antibodies to such proteins are useful as highly specific diagnostic agents capable of detecting of human hepatitis B virus from HCC to detect this virus from patients who are carriers of hepatitis B surface antigen who may then be at risk of developing HCC. The proteins, or antibodies of such proteins can be used as a material for development of prophylactic and therapeutic vaccines against this viral strain.

It is well known that one or more nucleotides in a DNA sequence can be substituted by other nucleotides to produce the same protein. The present invention also concerns such nucleotide changes which code for proteins reported in this invention. It is equally well known that one or more amino acids in a protein sequence can be replaced by other analogous amino acids, as defined by their hydrophilic properties or charges, to produce an analog of the amino acid sequence. Any analogs of the proteins of the present invention involving amino acid replacement, deletions, isosteres (modified amino acids that bear close structural and spatial similarity to protein amino acids), or additions, can be utilized, provided that the resulting sequences elicit antibodies recognizing hepatitis B virus from HCC with a mutation at amino acid is mutation 133 (Methionine to Threonine) of the major surface antigen.

EXAMPLES

The nucleotide sequence and the deduced amino acid sequence of human hepatitis B virus, isolated from HCC and carrying a mutation at amino acid residue 133 (Methionine to Threonine) of the major surface antigen, were determined in the following manner:

1. Isolation of Viral DNA

The viral DNA was isolated from a serum sample (5194) obtained from a 63-year old Chinese female patient of surface antigen carrier. She was confirmed as an HCC patient by biopsy. The hepatitis B virus from her serum carried a mutation at amino acid residue 133 (Methionine to Threonine) in the major surface antigen, as shown by our previous sequencing analysis o; the "a" epitope.

The isolation method used was:

200 μl of the serum sample was added with 400 μl of the lysis buffer (Tris chloride 10 mM, pH7.4, EDTA 1 mM, and sodium dodecyl sulfate 2%) and 25 μl of proteinase K (20 mg/ml), incubated at 65° C. for 3 hours. Viral DNA was then extracted by phenol/chloroform and precipitated by ethanol.

2. Amplification of Viral DNA by Polymerase Chain Reaction (PCR)

Figure 2:
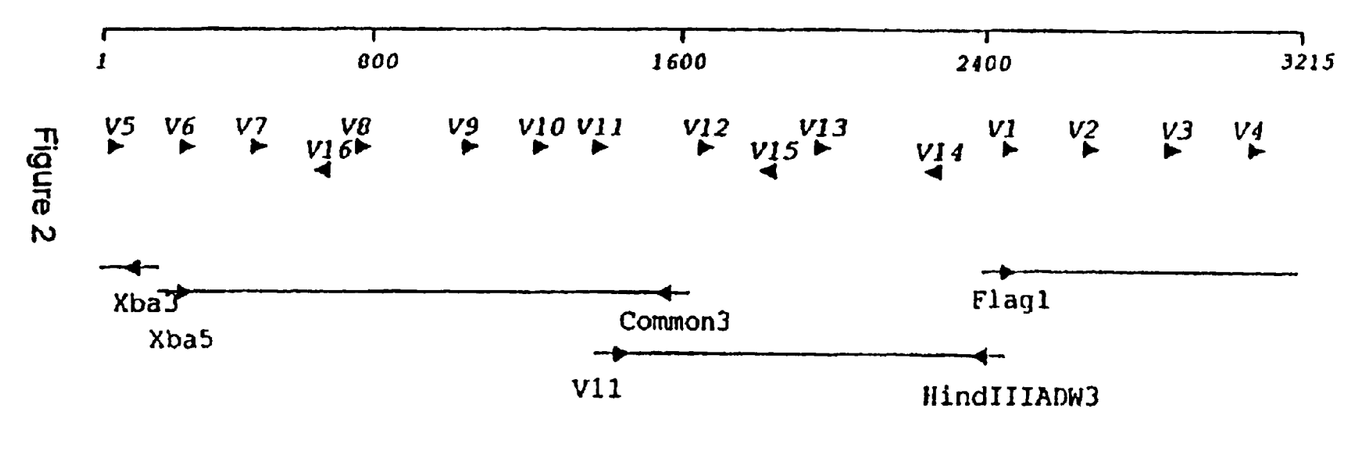
FIG. 2. Strategy of cloning and sequence determination of the same hepatitis B viral genome.

The virus genome in the present invention was amplified by polymerase chain reaction (PCR) using 3 sets of overlapping oligonucleotides, which were designed according to the wild type hepatitis B virus. Various restriction enzyme sites were included to facilitate the cloning of the PCR products. The position of these oligonucleotides is shown in FIG. 2 and indicated as follows:

Flag 1 (AT AAGCTTATGCCCCTATCTTATCAACACTTCCGGA) (SEQ. I.D. No. 6) starts at the initiation site of the coding region of DNA polymerase, at position 2307 of the viral nucleotide sequence and matches the coding strand (sense oligonucleotide). An additional HindIII restriction enzyme site is underlined;

Xba3 (GAGTCTAGACTCTGCGGTATTGTGA) (SEQ. I.D. No. 7) starts at the internal restriction enzyme site XbaI, at position 250 of the viral nucleotide sequence and matches the complementary strand (anti-sense oligonucleotide). An additional XbaI restriction enzyme site is underlined;

Xba5 (GAGTCTAGACTCGTGGTGGACTTCT) (SEQ. I.D. No. 8) starts at the internal XbaI site, at the same location as that of Xba3 oligonucleotide but matches the coding strand (sense oligonucleotide). An additional XbaI restriction enzyme site is underlined;

Common 3 (TGAGAATTCTCACGGTGGTCTCCATGCGACGT) (SEQ. I.D. No. 9) starts at the stop codon of the DNA polymerase, at position 1623 of the viral nucleotide sequence and matches the complementary strand (anti-sense oligonucleotide). An additional EcoRI restriction enzyme site is underlined;

V11 (TTTGTTTACGTCCCGT) (SEQ. I.D. No. 10) starts near the initiation site of the X gene, at position 1420 of the viral nucleotide sequence and matches the coding strand (sense oligonucleotide);

HindIIIADW3 (CTAAGCTTAGTTTCCGGAAGTGTTGAT) (SEQ. I.D. No. 11) starts close to the initiation site of the DNA polymerase, at position 2340 and matches the complementary strand (anti-sense oligonucleotide). An additional HindIII restriction enzyme site is underlined.

Using viral DNA as template, PCR was then carried out on a DNA Thermal Cycler (Perkin-Elmer. Cetus) for 35 cycles using Pfu polymerase (Stratagene, U.S.A.), each cycle consisting of 1.5 minutes at a denaturing temperature of 94° C., 2 minutes at an annealing temperature of 53° C. and 4 minutes at an extension temperature of 72° C. The following combinations of oligonucleotides were used: Flag1/Xba3, Xba5/Common3 and V11/HindIIIADW3, and generated amplification products of 1.2 kb, 1.4 kb and 1.1 kb respectively.

3. Cloning of the Amplified Viral DNA Fragments

The amplified viral DNA fragment from Flag1/Xba3 (1.2 kb) was subjected to restriction enzyme digestion by HindIII and XbaI, prior to cloning in a BlueScript plasmid pre-treated by the same restriction enzymes. Similar digestion with XbaI and EcoRI was applied to PCR product from Xba5/Common3 (1.4 kb), prior to cloning in a BlueScript plasmid pre-treated by XbaI and EcoRI. On the other hand, the DNA fragment amplified with V11 and HindIIIADW3 (1.1 kb) was directly cloned into a ZeroBlunt plasmid, developed by InvitroGen (U.S.A.) for cloning blunt-end DNA fragments.

4. Determination of Nucleotide Sequence

Nucleotide sequence of the human hepatitis B virus isolated from HCC and reported in the present invention was determined on plasmid DNA template by chain-terminating inhibitors, using the Sequenase DNA Sequencing Kit (United States Biochemical Corp.). To facilitate the sequencing procedure, various internal oligonucleotides were designed (from V1 to V16) according to the wild type hepatitis B virus, and their positions are indicated in FIG. 2.

From the analysis described above, the full-length nucleotide sequence of the hepatitis B virus, isolated from HCC and carrying a mutation at amino acid residue 133 (Methionine to Threonine) of the major surface antigen, was determined. The amino acid sequence coding for the major viral proteins hepatitis B viral DNA polymerase, the large surface antigen, including the middle and major surface antigen, the core protein and the trans-activating X protein were deduced.

Alignment of the virus sequence in the present invention with other hepatitis B viral sequences, available in the Genbank database, will point to specific sequence differences which in turn can be used to design DNA probes. A detection system using polymerase chain reaction (PCR) can then be developed. Such PCR reactions will involve combinations of oligonucleotides specific to human hepatitis B virus in the present invention, with a mutation at the amino acid residue 133 (Methionine to Threonine) of the major surface antigen, thereby allowing highly specific detection of these mutant viral DNA. Briefly, viral DNA can be extracted as described in this invention. PCR reaction can be performed using specific oligonucleotides using the similar cycling conditions described above. Results can then be analyzed after resolving PCR products on a 1% agarose gel.

According to known immunological procedures, it is possible to determine epitopes from protein sequences as those in FIGS. 4–7. Determination of these epitopes specific to human hepatitis B virus, from HCC and carrying a mutation at amino acid residue 133 (Methionine to Threonine) of the major surface antigen, will allow synthesis of peptides using known genetic engineering methods, synthesis of proteins, production of antibodies specific to these epitopes, development of specific diagnostic reagents, development of prophylactic and therapeutic vaccines, and antiviral agents.

A detection system for antibody against hepatitis B virus isolated from HCC and carrying a mutation at amino acid residue 133 (Methionine to Threonine) of the major surface antigen can be developed using polyvinyl microtiter plates and the sandwich method. Briefly, 50 μl of 5 μg/ml concentration of a peptide from the hepatitis B virus in the present invention, isolated from HCC and carrying a mutation at amino acid residue 133 (Methionine to Threonine) of the major surface antigen, can be dispensed in each well of the microtiter plates and incubated overnight at room temperature for consolidation. A similar procedure can be applied to a protein purified from host cells such as Escherichia coli. The microplate wells can be washed five times with physiological saline solution containing 0.05% Tween 20. For overcoating, 100 µl of NaCl buffer containing 30% (v/v) of calf serum and 0.05% Tween 20 (CS buffer) can be dispensed in each well and discarded after incubation for 30 minutes at room temperature.

To determine antibodies specific for the mutant (Methionine to Threonine at amino acid residue 133 of the major surface antigen) hepatitis B virus in serum, the primary reaction can be carried out such that 50 µl of the CS buffer and 10 µl of a serum sample can be dispensed in each microplate well and incubated on a microplate vibrator for one hour at room temperature. After completion of the primary reaction, microplate wells are washed five times as described above.

In the secondary reaction, 1 ng of horseradish peroxidase labeled anti-human IgG mouse monoclonal antibodies dissolved in 50 µl of calf serum can be dispensed in each microplate well and incubated on a microplate vibrator for one hour at room temperature. Upon completion, wells can be washed five times in the same way. After addition of hydrogen peroxide (as substrate) and 50 µl of O-phenylenediamine solution (as color developer) in each well, and after incubation for 30 minutes at room temperature, 50 µl of 4M sulphuric acid solution can be dispensed in each well to stop further color development and for reading absorbance at 490 nm.

The present invention makes possible detection of the mutant human hepatitis B virus, in particular those carrying a mutation at amino acid residue 133 (Methionine to Threonine) of the major surface antigen. The present invention also provides detection systems capable of a highly specific and sensitive detection at an early stage of infection or development of HCC when the HCC may be treated and cured.

In addition, these features allow accurate diagnosis of patients at an early stage in the HCC and also help to inhibit with higher efficiency mutant hepatitis B virus.

Proteins and their antibodies under the present invention can be utilized for development of prophylactic and therapeutic vaccines, as well as, immunological pharmaceuticals. Sequence information on structural genes of these mutant viruses will be helpful for developing detection systems of the relevant protein antigens and antibodies.

Antigen-antibody complexes can be detected by known methods. Specific monoclonal and polyclonal antibodies can be raised by immunizing animals such as mice and rabbits with peptides or proteins specific to mutant hepatitis B viruses from HCC. Inhibitory antiviral agents can be designed and targeted against these proteins and molecules in cell culture or in vivo.

The present invention is based on studies on human hepatitis virus genome isolated from HCC and carrying a mutation at amino acid residue 133 (Methionine to Threonine) of the major surface antigen. The invention makes possible highly specific detection of these mutant hepatitis B virus from HCC, and provides material such as protein, polyclonal and monoclonal antibodies for development of such detection system.

References

1. Oon, C-J., "Viral hepatitis B in Singapore: epidemiology, prevention and control-monitoring the hepatitis B programme and management of carriers" *J. Royal College Physic. London* (1997), in press.
2. Ogata, N., et al. "Infectivity and pathogenicity in chimpanzees of a surface gene mutant of hepatitis B virus that emerged in a vaccinated infant" *J. Infec. Disease* (1997) 175: 511–523.
3. Oon, C-J., "Issues associated with HBV mutant strains" *J. Royal College Physic. London* (1997), in press.
4. Oon, C-J., et al. "Hepatitis B surface antigen (HBsAg) mutants—their significance" *Annals Acad. Med. Sincapore* (1997), in press.
5. Tsai, J. F., et al. "Additive effect modification of hepatitis B surface antigen and e antigen on the development of hepatocellular carcinoma" *Brit. J. Cancer* (1996) 73: 1498–1502.
6. Oon, C-J., "Molecular epidemiology of hepatitis B 'a' variants and mutants: significance in immune population" *JAMA* (1996) 12: pp.5–6.
7. Goh, K-T, "Hepatitis B immunization in Singapore" *Lancet* (1996) 348: 1385–1386.
8. Oon, C-J., et al., "Natural history of hepatitis B surface antigen mutants in children" *Lancet* (1996) 348: 1524–1525.
9. Harrison, T. J., "Genetic variation in hepatitis B virus" *Eur. J. Gastroenter. & Hepatol.* (1996) 8: pp.306–311.
10. Oon, C-J., et al., "Molecular epidemiology of hepatitis B virus vaccine variants in Singapore" *Vaccine* (1995) 13: 699–702.
11. Oon, C-J., et al. "Molecular epidemiology of hepatitis B variants and mutants—significance and transmissibility" *Proc.3nd Internatl. Symp. Viral Hepatitis & HCC, Singapore* (1995) pp.39–43.
12. Carman, W., et al., "Viral genetic variation: hepatitis B virus as a clinical example" *Lancet* (1993) 341: 349–353.
13. Harrison, T. J., "Variants of hepatitis B virus" *Vox Sane* (1992) 63: 161–167.
14. Carman, W. F., et al., "Vaccine-induced escape mutant of hepatitis B virus" *Lancet* (1990) 336: 325–329.

What is claimed is:

1. An isolated polypeptide comprising amino acid residues 174 through 400 of SEQ ID NO.:3.

2. An isolated peptide comprising amino acid residues 298 through 320 of SEQ ID NO.:3.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 3215 base pairs
      (B) TYPE: nucleic acid (C) STRANDEDNESS: double
(D) TOPOLOGY: circular (xi) SEQUENCE DESCRIPTION: SEQ ID NO: 1:

```
CTCCACAACA TTCCACCAAG CTCTGCTAGA TCCCAGGGTG AGGGGCCTAT ATTTTCCTGC      60
TGGTGGCTCC AGTTCCGGAA CAGTAAACCC TGTTCCGACT ACTGCCTCTC CCATATCGTC     120
AATCTTCTCG AGGACTGGGG ACCCTGCACC GAACATGGAG AACACAACAT CAGGATTCCT     180
AGGACCCCTG CTCGTGTTAC AGGCGGGGTT TTTCTCGTTG ACAAGAATCC TCACAATACC     240
GCAGAGTCTA GACTCTGGTG GACTTCTCTC AATTTTCTAG GGGGAGCACC CACGTGTTCC     300
TGGCCAAAAT TCGCAGTCCC CAACCTCCAA TCACTCACCA ACCTCTTGTC CTCCAATTTG     360
TCCTGGCTAT CGCTGGATGT GTCTGCGGCG TTTTATCATA TTCCTCTTCA TCCTGCTGCT     420
ATGCCTCATC TTCTTGTTGG TTCTTCTGGA CTACCAAGGT ATGTTGCCCG TTTGTCCTCT     480
ACTTCCAGGA ACATCAACCA CCAGCACGGG GCCATGCAAG ACCTGCACGA CTCCTGCTCA     540
AGGAAACTCT ACGTTTCCCT CTTGTTGCTG TACAAAACCT TCGGACGGAA ACTGCACTTG     600
TATTCCCATC CCATCATCCT GGGCTTTCGC AAGATTCCTA TGGGAGTGGG CCTCAGTCCG     660
TTTCTCCTGG CTCAGTTTAC TAGTGCCATT TGTTCAGTGG TTCGTAGGGC TTTCCCCCAC     720
TGTTTGGCTT TCAGTTATAT GGATGATGTG GTATTGGGGG CGAAGTCTGT ACAACATCTT     780
GAGTCCCTTT TTACCTCTAT TACCAATTTT CTTTTGTCTT TGGGTATACA TTTAAACCCT     840
AATAAAACCA AACGTTGGGG CTACTCCCTT AACTTCATGG GATATGTAAT TGGAAGTTGG     900
GGTACTTTAC CGCAGGAACA TATTGTACTA AAACTCAAGC AATGTTTTCG AAAACTGCCT     960
GTAAATAGAC CTATTGATTG GAAAGTATGT CAAAGAATTG TGGGTCTTTT GGGCTTTGCT    1020
GCCCCTTTTA CACAATGTGG CTATCCTGCC TTGATGCCTT TATATGCATG TATACAATCT    1080
AAGCAGGCTT TCACTTTCTC GCCAACTTAC AAGGCCTTTC TGTGTAAACA ATATCTGAAC    1140
CTTTACCCCG TTGCCCGGCA ACGGTCCGGT CTCTGCCAAG TGTTTGCTGA CGCAACCCCC    1200
ACTGGATGGG GCTTGGCCAT AGGCCATCAG CGCATGGCTG GAACCTTTCT GGCTCCTCTG    1260
CCGATCCATA CTGCGGAACT CCTAGCAGCT TGTTTTGCTC GCAGCCGGTC TGGAGCAAAA    1320
CTTATCGGAA CCGACAACTC TGTTGTCCTC TCTCGGAAAT ACACCTCCTT TCCATGGCTG    1380
CTAGGGTGTG CTGCCAACTG GATCCTGCGC GGGACGTCCT TTGTCTACGT CCCGTCGGCG    1440
CTGAATCCCG CGGACGACCC GTCTCGGGGC CGTTTGGGGC TCTACCGTCC CCTTCTTCAT    1500
CTGCCGTTCC GGCCGACCAC GGGGCGCACC TCTCTTTACG CGGTCTCCCC GTATGTGCCT    1560
TCTCATCTGC CGGACCGTGT GCACTTCGCT TCACCTCTGC ACGTCGCATG GAGACCACCG    1620
TGAACGCACG CCAGGTCTTG CCCAAGGTCT TATATAAGAG GACTCTTGGA CTCTCAGCAA    1680
TGTCAACGAC CGACCTTGAG GCATACTTCA AAGACTGTGT GTTTAAAGAC TGGGAGGAGT    1740
TGGGGGAGGA GATTAGGTTA AAGATTTATG TACTAGGAGG CTGTAGGCAT AAATTGGTCT    1800
GTTCACCAGC ACCATGCAAC TTTTTCTCCT CTGCCTAATC ATCTCATGTT CATGTCCTAC    1860
TGTTCAAGCC TCCAAGCTGT GCCTTGGGTG GCTTTGGGAC ATGGACATTG ACCCGTATAA    1920
AGAATTTGGA GCATCTGCTG AGTTACTCTC TTTTTTGCCT TCTGACTTCT TTCCGTCTAT    1980
TCGAGATCTC CTCGACACCG CCTCTGCTCT GTATCGGGAG GCCTTAGAGT CTCCGGAACA    2040
TTGTTCGCCT CACCATACAG CACTCAGGCA AGCTATTTTG TGTTGGGGTG AGTTGATGAA    2100
TCTGGCCACC TGGGTGGGAA GTAAATTTGGA AGATCCAGCA TCCAGGGAAT TAGTAGTCAG    2160
CTATGTCAAC GTTAATATGG GCCTAAAACT CAGACAAATA TTGTGGTTTC ACATTTCCTG    2220
```

-continued

```
TCTTACTTTT GGAAGAGAAA CTGTTCTTGA GTACTTGGTA TCTTTTGGAG TGTGGATTCG    2280

CACTCCTACC GCTTACAGAC CACCAAATGC CCCTATCTTA TCAACACTTC CGGAAACTAC    2340

TGTTGTTAGA CGACGAGGCA GGTCCCCTAG AAGAAGAACT CCCTCGCCTC GCAGACGAAG    2400

GTCTCAATCG CCGCGTCGCA GAAGATCTCA ATCTCGGGAA TCTCAACGTT AGTATTCCTT    2460

GGACTCATAA GGTGGGAAAC TTTACTGGGC TTTATTCTTC TACTGTACCT GTCTTTAATC    2520

CCGAGTGGCA AATTCCTTCC TTTCCTCACA TTCATTTACA AGAGGACATT ATTAATAGAT    2580

GTCAACAATA TGTGGGCCCT CTTACAGTTA ATGAAAAAAG AAGATTAAAA TTAATTATGC    2640

CTGCTAGGTT TTATCCTAAC CTTACTAAAT ATTTGCCCTT AGACAAAGGC ATTAAACCGT    2700

ATTATCCTGA ACATGCAGTT AATCATTACT TCAAAACTAG GCATTATTTA CATACTCTGT    2760

GGAAGGCTGG CATTCTATAT AAGAGAGAAA CTACACGCAG CGCCTCATTT TGTGGGTCAC    2820

CATATTCTTG GAACAAGAG CTACAGCATG GGAGGTTGGT CTTCCAAACC TCGACAAGGC    2880

ATGGGGAGCA ATCTTGCTGT TCCCAATCCT CTGGGATTCT TTCCCGATCA CCAGTTGGAC    2940

CCTGCGTTCG GAGCCAACTC AAACAATCCA GATTGGGACT TCAACCCCAA CAAGGATCAC    3000

TGGCCAGAGG CAAATCAGGT AGGAGTGGGA GCATTCGGGC CAGGGTTCAC CCCACCACAC    3060

GGCGGTCTTT TGGGGGGGAG CCCTCAGGCT CAGGGCATAT TGACAACAGT GCCAGCAGCA    3120

CCTCCTCCTG CCTCCACCAA TCGGCAGTCA GGAAGACAGC CTACTCCCAT CTCTCCACCT    3180

CTAAGAGACA GTCATCCTCA GGCCACGCAG TGGAA                               3215
```

(2) INFORMATION FOR SEQ ID NO: 2:

(i) SEQUENCE CHARACTERISTICS:
      (A) LENGTH: 843 amino acids
      (B) TYPE: amino acid
      (C) STRANDEDNESS: single
      (D) TOPOLOGY: linear (xi) SEQUENCE DESCRIPTION: SEQ ID NO: 2:

```
Met Pro Leu Ser Tyr Gln His Phe Arg Lys Leu Leu Leu Leu Asp Asp
1               5                   10                  15

Glu Ala Gly Pro Leu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Ile Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
```

-continued

```
                180              185              190
Gly Asp Glu Ser Cys Cys Ser Gln Ser Ser Gly Ile Leu Ser Arg Ser
            195                      200                      205
Pro Val Gly Pro Cys Val Arg Ser Gln Leu Lys Gln Ser Arg Leu Gly
210                      215                      220
Leu Gln Pro Gln Gln Gly Ser Leu Ala Arg Gly Lys Ser Gly Arg Ser
225                      230                      235                      240
Gly Ser Ile Arg Ala Arg Val His Pro Thr Thr Arg Arg Ser Phe Gly
                    245                      250                      255
Gly Glu Pro Ser Gly Ser Gly His Ile Asp Asn Ser Ala Ser Ser Thr
                260                      265                      270
Ser Ser Cys Leu His Gln Ser Ala Val Arg Lys Thr Ala Tyr Ser His
            275                      280                      285
Leu Ser Thr Ser Lys Arg Gln Ser Ser Ser Gly His Ala Val Glu Leu
290                      295                      300
His Asn Ile Pro Pro Ser Ser Ala Arg Ser Gln Gly Glu Gly Pro Ile
305                      310                      315                      320
Phe Ser Cys Trp Trp Leu Gln Phe Arg Asn Ser Lys Pro Cys Ser Asp
                    325                      330                      335
Tyr Cys Leu Ser His Ile Val Asn Leu Leu Glu Asp Trp Gly Pro Cys
                340                      345                      350
Thr Glu His Gly Glu His Asn Ile Arg Ile Pro Arg Thr Pro Ala Arg
            355                      360                      365
Val Thr Gly Gly Val Phe Leu Val Asp Lys Asn Pro His Asn Thr Ala
370                      375                      380
Glu Ser Arg Leu Trp Trp Thr Ser Leu Asn Phe Leu Gly Gly Ala Pro
385                      390                      395                      400
Thr Cys Ser Trp Pro Lys Phe Ala Val Pro Asn Leu Gln Ser Leu Thr
                    405                      410                      415
Asn Leu Leu Ser Ser Asn Leu Ser Trp Leu Ser Leu Asp Val Ser Ala
                420                      425                      430
Ala Phe Tyr His Ile Pro Leu His Pro Ala Ala Met Pro His Leu Leu
            435                      440                      445
Val Gly Ser Ser Gly Leu Pro Arg Tyr Val Ala Arg Leu Ser Ser Thr
450                      455                      460
Ser Arg Asn Ile Asn His Gln His Gly Ala Met Gln Asp Leu His Asp
465                      470                      475                      480
Ser Cys Ser Arg Lys Leu Tyr Val Ser Leu Leu Leu Tyr Lys The
                    485                      490                      495
Phe Gly Arg Lys Leu His Leu Tyr Ser His Pro Ile Ile Leu Gly Phn
                500                      505                      510
Arg Lys Ile Pro Met Gly Val Gly Leu Ser Pro Phe Leu Leu Ala Gls
            515                      520                      525
Phe Thr Ser Ala Ile Cys Ser Val Val Arg Arg Ala Phe Pro His Cyl
530                      535                      540
Leu Ala Phe Ser Tyr Met Asp Asp Val Val Leu Gly Ala Lys Ser Var
545                      550                      555                      560
Gln His Leu Glu Ser Leu Phe Thr Ser Ile Thr Asn Phe Leu Leu Ser
                    565                      570                      575
Leu Gly Ile His Leu Asn Pro Asn Lys Thr Lys Arg Trp Gly Tyr Sen
                580                      585                      590
Leu Asn Phe Met Gly Tyr Val Ile Gly Ser Trp Gly Thr Leu Pro Gln
595                      600                      605
```

```
Glu His Ile Val Leu Lys Leu Lys Gln Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
                660                 665                 670

Tyr Lys Ala Phe Leu Cys Lys Gln Tyr Leu Asn Leu Tyr Pro Val Ala
                675                 680                 685

Arg Gln Arg Ser Gly Leu Cys Gln Val Phe Ala Asp Ala Thr Pro Thr
                690                 695                 700

Gly Trp Gly Leu Ala Ile Gly His Gln Arg Met Ala Gly Thr Phe Leu
705                 710                 715                 720

Ala Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
                740                 745                 750

Leu Ser Arg Lys Tyr Thr Ser Phe Pro Trp Leu Leu Gly Cys Ala Ala
                755                 760                 765

Asn Trp Ile Leu Arg Gly Thr Ser Phe Val Tyr Val Pro Ser Ala Leu
770                 775                 780

Asn Pro Ala Asp Asp Pro Ser Arg Gly Arg Leu Gly Leu Tyr Arg Pro
785                 790                 795                 800

Leu Leu His Leu Pro Phe Arg Pro Thr Thr Gly Arg Thr Ser Leu Tyr
                805                 810                 815

Ala Val Ser Pro Tyr Val Pro Ser His Leu Pro Asp Arg Val His Phe
                820                 825                 830

Ala Ser Pro Leu His Val Ala Trp Arg Pro Pro
                835                 840

(2) INFORMATION FOR SEQ ID NO: 3:

(i) SEQUENCE CHARACTERISTICS:
        (A) LENGTH: 400 amino acids
        (B) TYPE: amino acid
        (C) STRANDEDNESS: single
        (D) TOPOLOGY: linear (xi) SEQUENCE DESCRIPTION: SEQ ID NO: 3:

Met Gly Gly Trp Ser Ser Lys Pro Arg Gln Gly Met Gly Thr Asn Leu
1               5                   10                  15

Ala Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
            35                  40                  45

Lys Asp His Trp Pro Glu Ala Asn Gln Val Gly Val Gly Ala Phe Gly
    50                  55                  60

Pro Gly Phe Thr Pro Pro His Gly Gly Leu Leu Gly Ser Pro Gln
65              70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
                100                 105                 110

Arg Asp Ser His Pro Gln Ala Thr Gln Trp Asn Ser Thr Thr Phe His
```

-continued

```
            115                 120                 125
Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
                180                 185                 190

Phe Phe Ser Leu Thr Arg Ile Leu Thr Ile Pro Gln Ser Leu Asp Ser
                195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Asn Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Leu Pro Gly Thr Ser
    275                 280                 285

Thr Thr Ser Thr Gly Pro Cys Lys Thr Cys Thr Thr Pro Ala Gln Gly
    290                 295                 300

Asn Ser Thr Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Val
    355                 360                 365

Ile Trp Met Met Trp Tyr Trp Gly Arg Ser Leu Tyr Asn Ile Leu Ser
    370                 375                 380

Pro Phe Leu Pro Leu Leu Pro Ile Phe Phe Cys Leu Trp Val Tyr Ile
385                 390                 395                 400
```

(2) INFORMATION FOR SEQ ID NO: 4:

(i) SEQUENCE CHARACTERISTICS:
        (A) LENGTH: 212 amino acids
        (B) TYPE: amino acid
        (C) STRANDEDNESS: single
        (D) TOPOLOGY: linear     (xi) SEQUENCE DESCRIPTION: SEQ ID NO: 4:

```
Met Gln Leu Phe Leu Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
                20                  25                  30

Asp Pro Tyr Lys Glu Phe Gly Ala Ser Ala Glu Leu Leu Ser Phe Leu
            35                  40                  45

Pro Ser Asp Phe Phe Pro Ser Ile Arg Asp Leu Leu Asp Thr Ala Ser
        50                  55                  60

Ala Leu Tyr Arg Glu Ala Leu Glu Ser Pro Glu His Cys Ser Pro His
65                  70                  75                  80
```

```
His Thr Ala Leu Arg Gln Ala Ile Leu Cys Trp Gly Glu Leu Met Asn
            85                  90                  95

Leu Ala Thr Trp Val Gly Ser Asn Leu Glu Asp Pro Ala Ser Arg Glu
            100                 105                 110

Leu Val Val Ser Tyr Val Asn Val Asn Met Gly Leu Lys Leu Arg Gln
            115                 120                 125

Ile Leu Trp Phe His Ile Ser Cys Leu Thr Phe Gly Arg Glu Thr Val
130                 135                 140

Leu Glu Tyr Leu Val Ser Phe Gly Val Trp Ile Arg Thr Pro Thr Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Arg
210

(2) INFORMATION FOR SEQ ID NO: 5:

(i) SEQUENCE CHARACTERISTICS:
        (A) LENGTH: 154 amino acids
        (B) TYPE: amino acid
        (C) STRANDEDNESS: single
        (D) TOPOLOGY: linear (xi) SEQUENCE DESCRIPTION: SEQ ID NO: 5:

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
            20                  25                  30

Pro Phe Gly Ala Leu Pro Ser Pro Ser Ser Ala Val Pro Ala Asp
            35                  40                  45

His Gly Ala His Leu Ser Leu Arg Gly Leu Pro Val Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala Arg Gln Val Leu Pro Lys Val Leu Tyr Lys Arg
            85                  90                  95

Thr Leu Gly Leu Ser Ala Met Ser Thr Thr Asp Leu Glu Ala Tyr Phe
            100                 105                 110

Lys Asp Cys Val Phe Lys Asp Trp Glu Glu Leu Gly Glu Glu Ile Arg
            115                 120                 125

Leu Lys Ile Tyr Val Leu Gly Gly Cys Arg His Lys Leu Val Cys Ser
130                 135                 140

Pro Ala Pro Cys Asn Phe Phe Ser Ser Ala
145                 150

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 6:
```

```
ATAAGCTTAT GCCCCTATCT TATCAACACT TCCGGA                           36

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 7:

GAGTCTAGAC TCTGCGGTAT TGTGA                                       25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 8:

GAGTCTAGAC TCGTGGTGGA CTTCT                                       25

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 9:

TGAGAATTCT CACGGTGGTC TCCATGCGAC GT                               32

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 10:

TTTGTTTACG TCCCGT                                                 16

(2) INFORMATION FOR SEQ ID NO: 11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 11:

ATAAGCTTAT GCCCCTATCT TATCAACACT TCCGGA                           36
```